US008831773B2

(12) United States Patent
Rosenbaum

(10) Patent No.: US 8,831,773 B2
(45) Date of Patent: Sep. 9, 2014

(54) SYSTEMS AND METHODS FOR AUTOMATING PHARMACY OPERATIONS UTILIZING ROBOTIC PICK AND PLACE TECHNOLOGY

(75) Inventor: Ronald Rosenbaum, Palm Harbor, FL (US)

(73) Assignee: MTS Medication Technologies, Inc., St. Petersburg, FL (US)

( * ) Notice: Subject to any disclaimer, the term of this patent is extended or adjusted under 35 U.S.C. 154(b) by 731 days.

(21) Appl. No.: 12/705,910

(22) Filed: Feb. 15, 2010

(65) Prior Publication Data

US 2011/0202171 A1     Aug. 18, 2011

(51) Int. Cl.
*G06F 7/00* (2006.01)
*G06F 19/00* (2011.01)
*B65B 35/18* (2006.01)
*B65B 5/10* (2006.01)

(52) U.S. Cl.
CPC ............ *G06F 19/3462* (2013.01); *B65B 35/18* (2013.01); *B65B 5/103* (2013.01)
USPC ........................................................ 700/216

(58) Field of Classification Search
USPC ....................................................... 700/216
See application file for complete search history.

(56) References Cited

U.S. PATENT DOCUMENTS

| 2002/0173875 | A1* | 11/2002 | Wallace et al. | 700/242 |
| 2006/0161293 | A1* | 7/2006 | William et al. | 700/216 |
| 2006/0259187 | A1 | 11/2006 | Berg | |
| 2007/0102109 | A1* | 5/2007 | Katritzky et al. | 156/277 |
| 2007/0150092 | A1* | 6/2007 | Ohmura et al. | 700/231 |
| 2008/0179387 | A1 | 7/2008 | Cantlay et al. | |
| 2008/0179389 | A1* | 7/2008 | Steinbacher | 235/375 |
| 2009/0281656 | A1 | 11/2009 | Draper | |

* cited by examiner

*Primary Examiner* — Ramya Burgess
(74) *Attorney, Agent, or Firm* — Robert J. Depke; The Chicago Technology Law Group, LLC

(57) ABSTRACT

The present invention is directed to a computer-controlled system for automatically transferring individual solid pharmaceutical products from bulk containers into a selected solid pharmaceutical product package from among a variety of different packaging solutions. Advantageously, in accordance with the preferred exemplary embodiment of the present invention, a robotic pick and place arm incorporates a contact holding mechanisms such as a suction tube which selectively temporarily secures a solid pharmaceutical product for transfer from a bulk container into a desired solid pharmaceutical product package.

12 Claims, 8 Drawing Sheets

SYSTEMS AND METHODS FOR AUTOMATING PHARMACY OPERATIONS UTILIZING ROBOTIC PICK AND PLACE TECHNOLOGY

BACKGROUND OF THE INVENTION

1. Field of the Invention

The present invention relates generally to the field of automated computer-controlled robotic systems. More specifically, the present invention is directed to computer-controlled robotic pick and place systems which are used for automating pharmacy operations.

2. Description of the Related Art

The tasks which are required to be performed by a pharmacist and/or assistant in a modern-day pharmacy have not been substantially changed for more than 50 years in regard to the transfer of solid pharmaceuticals from bulk containers into individual pill vials for a patient prescription. Today, in much the same way as was required 50 years ago, a pharmacist or technical assistant makes the appropriate transfer from a bulk container into an individual pill vial. While there have been a variety of advances relating to automatically counting an appropriate number of pills for transfer, this task continues to be a labor-intensive operation. Even today, in a modern pharmacy, a person is often required to manually count an appropriate number of individual solid pharmaceutical products for transfer from a bulk container to a patient prescription vial. There remains a significant potential for enhanced efficiency through automation of this process.

Another shortcoming and deficiency of existing pharmacy protocol is that primarily prescriptions for solid pharmaceutical products are transferred into a common pill vial for consumption by a patient. Particularly with an aging population, ever-increasing numbers of individuals are required to take numerous prescriptions throughout the day. It has long been recognized that alternate packaging solutions can be helpful in improving patient compliance with prescription requirements. Specifically, there are a wide variety of packaging solutions that are available in specific seven-day allotments or even multiple dosing times during a given day. In these existing conventional packaging solutions, an individual is provided with a separate package portion which incorporates all of a patient's prescriptions for a given dosing time or day.

Individuals can purchase these alternate packaging solutions but are required to manually transfer each different prescription from an individual pill vial into the appropriate separate package portion for a given dosing time or day. Existing pharmacy protocol would be significantly improved if it were possible for a patient to select a desired packaging solution without having to manually transfer solid pharmaceuticals from a pill vial that is only a temporary storage location. Currently there is no known solid pharmaceutical packaging solution which provides consumers with a convenient choice for the packaging of their pharmaceuticals.

While health care facilities have provided packaging solutions which eliminate the temporary transfer into individual pill vials, the machinery required for providing these known packaging solutions requires a substantial physical footprint and there is a significant financial investment in the machinery. As a result, these existing packaging systems have not been practical solutions for a neighborhood pharmacy.

Yet another shortcoming and deficiency of existing pharmacy protocol is that the pharmacist is often required to identify a number of different solid pharmaceutical products which have been co-mingled in a single container. Pharmacists regularly take the time to manually identify the pills for customer who is uncertain about the types of medications that have been commingled in a single container but this can be a time-consuming process and there is currently no convenient mechanism for automatically identifying and packaging a plurality of different prescriptions.

Accordingly, there remains a need in the art for improved automated packaging systems which can reduce the burden placed upon pharmacists and/or technical assistants in effecting the transfer of solid pharmaceutical products from bulk containers into individual patient specific product packaging. Additionally, there remains a need in the art for improved pharmacy protocol which can eliminate the unnecessary step of providing an intermediate patient specific product package from which solid pharmaceutical products are transferred into an alternate packaging solution.

There also remains a need for systems and methods which are capable of automatically identifying and packaging a random selection of different solid pharmaceutical products. The preferred embodiments of the present invention address these as well as other shortcomings and deficiencies of the prior art.

SUMMARY OF THE INVENTION

The present invention is directed to a computer-controlled system for automatically transferring individual solid pharmaceutical products from bulk containers into a selected solid pharmaceutical product package from among a variety of different packaging solutions. Advantageously, in accordance with the preferred exemplary embodiment of the present invention, a robotic pick and place arm incorporates a contact holding mechanisms such as a suction tube which selectively temporarily secures a solid pharmaceutical product for transfer from a bulk container into a desired solid pharmaceutical product package. The robotic arm is conveniently located preferably above a package filling location and a plurality of bulk solid pharmaceutical product containers are located adjacent the package filling location. The robotic arm, bulk containers and filling location are physically positioned so that the robotic pick and place arm can conveniently grab solid products from the bulk containers for placement into a desired product package location.

A computer controller for the robotic arm preferably receives patient prescription information and the computer dictates the movement of the robotic arm so that one or more of the appropriate solid pharmaceutical products is transferred from the bulk containers into the appropriate solid pharmaceutical product package locations corresponding to prescribed patient dosing times. During operation, the pharmacist and/or assistant receive notification concerning a patient prescription that is to be filled by the system. If a bulk container required for the new prescription is not already located on the machine, an appropriate bulk container is exchanged with one that is already located on the machine.

The robotic arm is then automatically controlled to transfer medications from the bulk containers to a desired product packaging solution. Advantageously, the patient is able to select the specific type of solid pharmaceutical product package that is desired. As detailed below, the system is capable of transferring one or more solid pharmaceuticals at a time in a single traverse of the robotic arm from a bulk container to the product package that is being filled.

In a first preferred exemplary embodiment of the present invention, the robotic arm which effects a transfer of individual solid pharmaceuticals from bulk containers into desired product packaging is programmed to maneuver from predetermined bulk storage locations to predetermined product package locations having specific product package cavity locations at predetermined fixed locations based upon the known placement of the packaging and its type. For example, those skilled in the art will appreciate that the robotic arm can be easily programmed to enter a bulk storage container having known dimensions at a predetermined location. A suction member or mechanical gripping device is then operated to secure an individual solid pharmaceutical product for transfer into packaging. The destination location is similarly programmed based upon stored information concerning physical parameters of known packaging types and the locations of desired product package cavities resulting from predetermined placement of the product package within the filling system. Patient prescription information is used to define a specific location into which a solid pharmaceutical product or nutraceutical product is to be placed.

In an alternate preferred exemplary embodiment of the present invention, some or all of the controlling for the robotic arm is based upon acquired digital image information. For example, one or more cameras are preferably incorporated into the system in order to more reliably locate and secure a solid pharmaceutical product. For example, a small digital imaging element may be incorporated into the robotic arm itself or physical structures adjacent thereto for monitoring the movement and positioning of the robotic arm relative to the bulk storage containers and the product package that is to be filled. In a particularly preferred exemplary embodiment of the present invention, a small digital imaging element is provided proximate the suction element and is secured to a portion of the moving robotic arm. In this alternate preferred exemplary embodiment, fine control of the movement of the robotic arm can be achieved for more reliably contacting an individual solid pharmaceutical product. Specifically, image information from this moving robotic camera can provide pill location information as well as orientation information in order to more reliably achieve contact and gripping of a solid pharmaceutical product. This is particularly useful when a bulk storage container is almost empty and particulate when it is necessary to secure a solid pharmaceutical product when only one or a limited number of individual solid pharmaceuticals or nutraceuticals are located at the bottom of a container.

Advantageously, this image information may also be stored and archived for confirming proper pill placement in a given patient's packaging. The archived information may include imaging of individual pill drops into specified cavities or a high-level view of the filled packaging.

Advantageously, in accordance with a preferred embodiment of the present invention, once the desired solid pharmaceutical product package has been completely filled in accordance with a patient's prescription, a machine vision system verifies that each of the appropriate solid pharmaceutical products have been transferred into their appropriate locations of the product package. Preferably, digital image information confirming the appropriate final state of the package is maintained to confirm that the patient has received the appropriate medicines.

In accordance with a first preferred exemplary embodiment of the present invention, an individual robotic pick and place arm transfers a single solid pharmaceutical product at a given time. In alternate preferred exemplary embodiment, a plurality of individual grabbing elements are provided on a common robotic arm with spacing that may be adjustable corresponding to at least one of either the pharmaceutical bulk storage locations and/or a desired solid pharmaceutical product packaging solution. Adventitiously, in accordance with this alternate preferred exemplary embodiment of the present invention, multiple product package locations are able to receive the appropriate solid pharmaceutical products during a single traverse of the robotic arm from the bulk container to the product package.

In accordance with another alternate preferred exemplary embodiment of the system, a flat surface or table may be provided adjacent to or at the location of the product package filling location. In accordance with this alternate embodiment of the present invention, the pharmacist or assistant is able to place a plurality of random pills for identification. An imaging system operating in conjunction with a computer having access to a database of solid pharmaceutical product physical characteristics compares the imaged physical characteristics of the solid pharmaceutical products to be identified so that the products can be automatically identified. The identified products may then be placed in packaging and the packaging then preferably receives an automatically appropriately printed label.

Advantageously, in accordance with a preferred exemplary embodiment of the present invention, a venting system and/or filtration system is provided which advantageously eliminates dust and the potential for cross-contamination as a result of fine particles of solid pharmaceutical material being incidentally separated from an individual solid pharmaceutical product. The venting and/or filtration system enables compliance with the relevant industry regulations in order to prevent cross contamination of pharmaceuticals handled by the system. In a preferred embodiment, the system may provide positive air pressure and a clean-room type environment within the system housing.

In accordance with another alternate preferred exemplary embodiment of the present invention, the pick and place robot selectively transfers a desired solid pharmaceutical product package from a storage location to a filling location based upon user selection. As a result, the patient is able to initially receive prescribed solid pharmaceutical product package in a desired format without having to transfer from an initially received pill vial.

DETAILED DESCRIPTION OF THE PRESENTLY PREFERRED EMBODIMENTS

Figure 1:
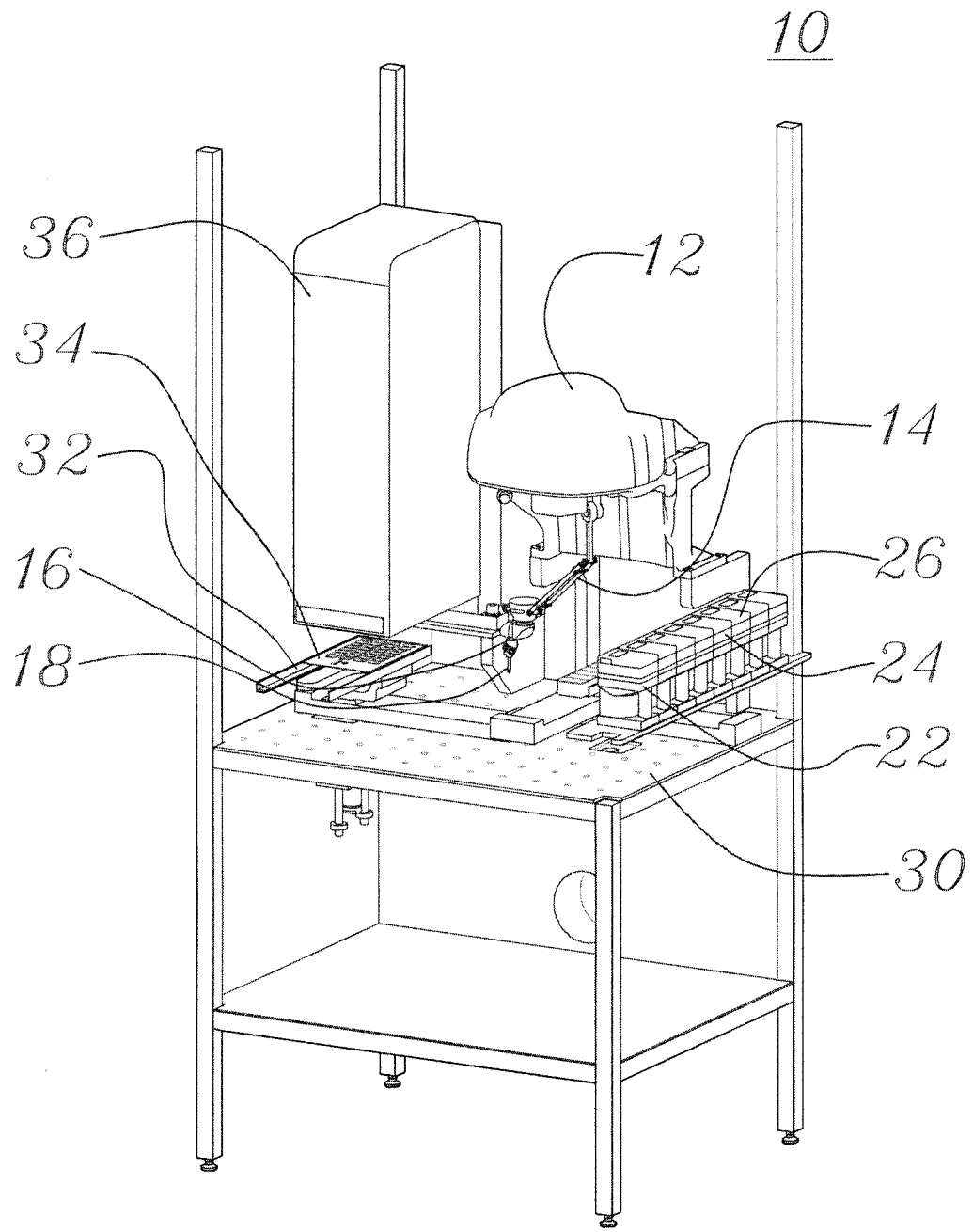
FIG. 1 illustrates a first exemplary embodiment of the present invention.

FIG. 1 illustrates a first preferred exemplary embodiment of the present invention which is shown generally at 10. In accordance with the preferred exemplary embodiment of the present invention, an automated robotic pick and place unit 12 is preferably centrally located in a housing. In accordance with the preferred exemplary embodiment of present invention, the outer walls of the housing which have not been shown for the sake of conveniently illustrating the device are preferably comprised of a clear material such as Plexiglas so that system operators can conveniently view the operations of the device. Additionally, the clear side walls of the structure provide an interesting and potentially entertaining view for individuals who are having their prescriptions filled.

The robotic arm 14 of the automated robotic pick and place unit 12 provides a traversing motion for a robotic joint 16 and contact pick and place element 18 which advantageously uses air suction for selectively holding and transferring a solid pharmaceutical product. In accordance with the present invention, a plurality of bulk solid pharmaceutical containers 22, 24, and 26 are conveniently located within the reach of the robotic arm 14 and contact pick and place element 18. The platform 30 upon which the structures are located includes a plurality of vent holes which facilitate venting which is described below.

A traversing platform 32 holds a solid pharmaceutical product package 34. In one embodiment, a system user places a product package 34 onto the traversing platform 32. In an alternate embodiment described below, the primary robotic arm pick and place unit or an alternate unit is used to selectively place a desired product package onto the traversing platform 32 as described below. The traversing platform 32 conveniently moves from a location beneath the automated robotic pick and place unit 12 to a location beneath and automated computer-controlled vision verification system 36.

In accordance with the preferred exemplary embodiment of the system, when a pharmacist or pharmacist assistant receives a prescription to be filled for a given patient, the necessary bulk solid pharmaceutical product container or containers such as those illustrated as elements 22, 24 or 26 is placed within the housing. Preferably, the system includes barcode or RFID verification of the bulk container prior to placing the bulk container in one of a plurality of preferably predetermined positions within the housing. After the system verifies that the requisite bulk container is present, the robotic arm rapidly transfers one or more solid pharmaceuticals from the bulk containers into the desired product package based upon electronically transferred patient prescription information that is stored in an electronic memory associated with the computer controller for the robotic arm.

In a first preferred exemplary embodiment of the present invention, robotic pick and place unit 12 which effects a transfer of individual solid pharmaceuticals from bulk containers into desired product packaging is programmed to maneuver from predetermined bulk storage locations 22, 24, 26 to predetermined product package locations 34 having specific product package cavity locations at predetermined fixed locations based upon the known placement of the packaging and its type. For example, those skilled in the art will appreciate that the robotic arm can be easily programmed to enter a bulk storage container having known dimensions at a predetermined location. A suction member or mechanical gripping device is then operated to secure an individual solid pharmaceutical product for transfer into packaging. The destination location is similarly programmed based upon stored information concerning physical parameters of known packaging types and the locations of desired product package cavities resulting from predetermined placement of the product package within the filling system. Patient prescription information is used to define a specific location into which a solid pharmaceutical product or nutraceutical product is to be placed.

In an alternate preferred exemplary embodiment of the present invention, some or all of the controlling for the robotic arm is based upon acquired digital image information. For example, one or more cameras are preferably incorporated into the system in order to more reliably locate and secure a solid pharmaceutical product. For example, a small digital imaging element may be incorporated into the robotic arm itself or physical structures adjacent thereto for monitoring the movement and positioning of the robotic arm relative to the bulk storage containers and the product package that is to be filled. In a particularly preferred exemplary embodiment of the present invention, a small digital imaging element is provided proximate the suction element and is secured to a portion of the moving robotic arm. In this alternate preferred exemplary embodiment, fine control of the movement of the robotic arm can be achieved for more reliably contacting an individual solid pharmaceutical product. Specifically, image information from this moving robotic camera can provide pill location information as well as orientation information in order to more reliably achieve contact and gripping of a solid pharmaceutical product. This is particularly useful when a bulk storage container is almost empty and particulate when it is necessary to secure a solid pharmaceutical product when only one or a limited number of individual solid pharmaceuticals or nutraceuticals are located at the bottom of a container.

Advantageously, this image information may also be stored and archived for confirming proper pill placement in a given patient's packaging. The archived information may include imaging of individual pill drops into specified cavities or a high-level view of the filled packaging.

After all of the prescribed patient doses have been transferred from the bulk containers into the product package 34, the traversing platform 32 may be moved to a location beneath the computer controlled electronic vision verification system 36. The electronic vision verification system 36 incorporates a digital camera which generates electronic image information that is used to confirm that all of the necessary medications have been placed into the appropriate package locations. An electronic memory associated with the electronic vision verification system stores image data pertaining to solid pharmaceutical pill physical characteristic information such as pill size, shape and color. The electronic vision verification system then compares the expected pill physical characteristic information from the database of pill physical characteristic information with the actual solid pharmaceutical physical characteristic data received from the electronic camera.

Based on this comparison, the system is able to confirm that all of the prescribed doses have been properly transferred into the appropriate locations of the product package. FIG. 1 illustrates the state of the system wherein the traversing platform 32 is located under the electronic image verification system 36 for confirming the system operations.

Figure 2:
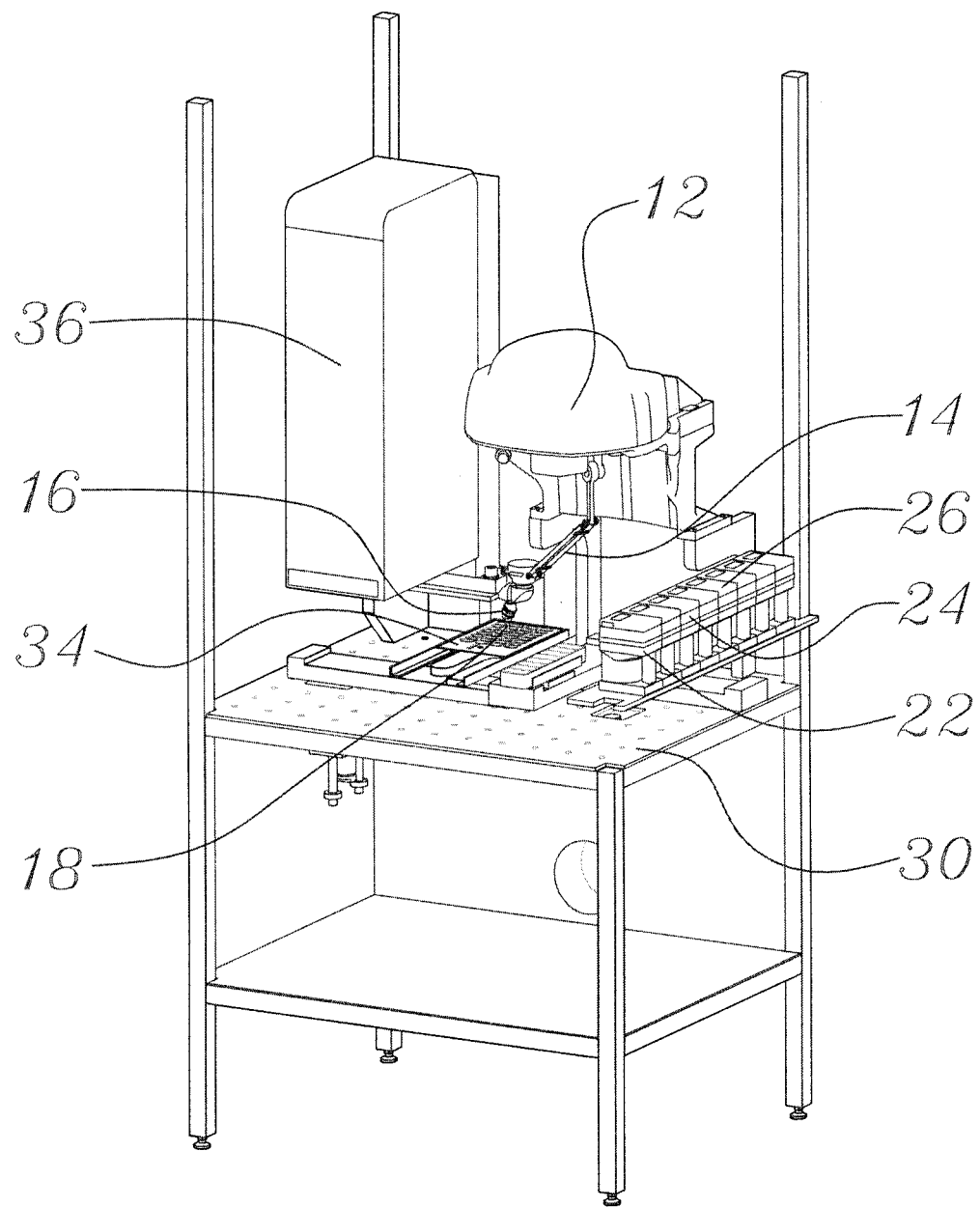
FIG. 2 illustrates an alternate view of the exemplary embodiment of the present invention illustrated in FIG. 1.

FIG. 2 illustrates the alternate state of the machine during the actual package filling operation. As noted above, during this stage of the operation, the package 34 is preferably located beneath the robotic pick and place unit 12 and the suction arm 18 moves from the bulk storage locations 22, 24, 26 in order to transfer solid pharmaceuticals into the package 34 in accordance with the electronically stored patient prescription information. It should be appreciated that the systems and methods of the present invention will revolutionize the operations of local pharmacy operations. In accordance with the systems and methods of the present invention, prescription data is electronically transferred to the system controller.

If the necessary bulk storage for prescribed patient doses is not present on the machine, the system operator is alerted via a computer monitor or other electronic communication to provide the appropriate bulk storage. Thereafter, the machine independently operates to automatically fill the patient prescription. The process is repeated to conveniently fill a significant volume of patient prescriptions with substantially reduced manual effort. The pharmacist or technician is only required to ensure that the required bulk containers are available and then to seal and label the finished package. A typical pharmacy is enabled to produce a significantly greater number of filled prescriptions.

Figure 3:
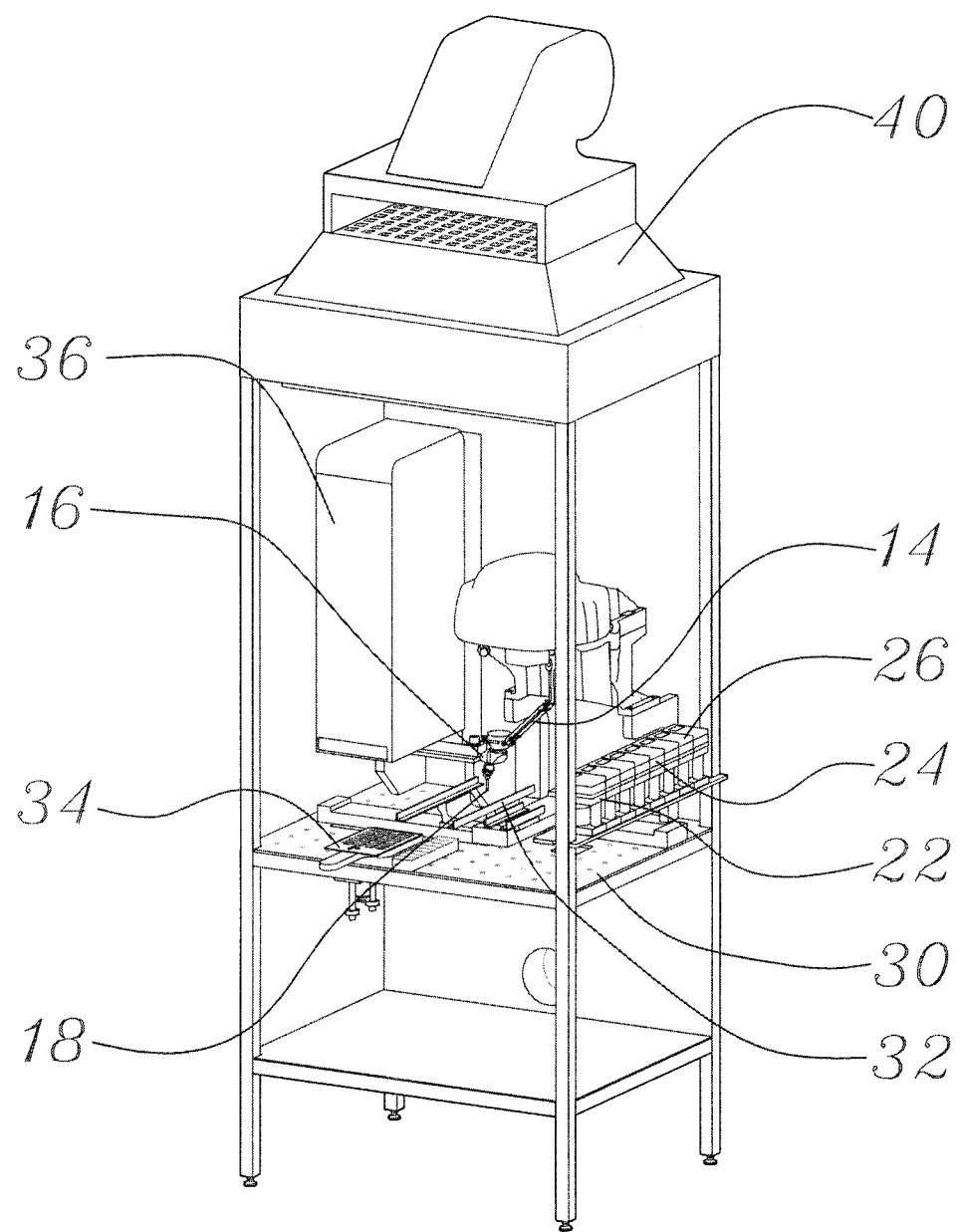
FIG. 3 illustrates additional features and aspects of the exemplary embodiment of the present invention.

FIG. 3 illustrates an embodiment of the invention wherein a blower structure 40 is provided to ensure proper venting and to remove any particulate matter or residue that may be generated from the handling of solid pharmaceutical products. As noted above, the platform 30 includes air transmission holes which facilitate exhausting of the enclosed system to remove the particles or residue and thereby eliminate any concerns about cross-contamination. The laminar flow hood provides an environment which prevents particles of drugs or other contaminants from dispersing into the atmosphere around the device or settling on containers or packages within the field of the machine. A combination of positive air flow from below the packaging surface in combination with a negative airflow or vacuum from above removes particulates from the area and passes them through a filter which removes them from the airflow.

Figure 4:
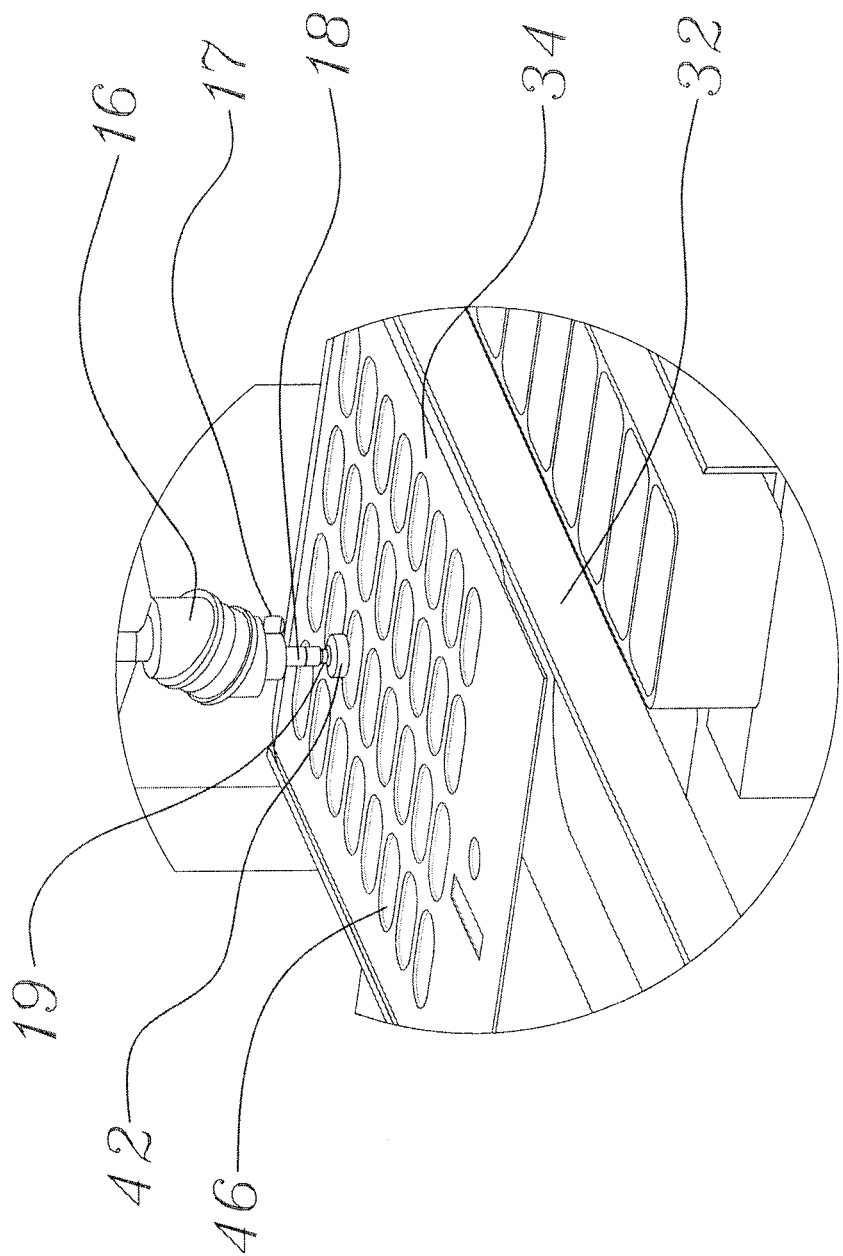
FIG. 4 illustrates the detailed operation of a robotic pick and place system used in filling pharmaceutical packaging.

FIG. 4 illustrates the detailed operation of the pill placement operation. As illustrated in FIG. 4, the traversing platform 32 has a package that is to be filled 34 and the traversing platform is preferably placed beneath the robotic pick and place unit 12 although this is not necessary and those skilled in the art will appreciate that other configurations are possible. The suction arm 18 has a solid pharmaceutical product 42 secured thereto and the arm is located above each of the product package cavities 46 for filling the cavities with the required solid pharmaceuticals. The transfer of solid pharmaceuticals from the bulk storage containers to the package cavities 46 is repeated until the patient prescription has been filled. The system is preferably programmed to accommodate filling a variety of different solid pharmaceutical package solutions from conventional pill vials or weekly package solutions with multiple dosing times.

FIG. 4 also illustrates the camera element 17 which traverses with the robotic arm and a suction element 19. As noted above, this camera element 17 may be used for physically acquiring a solid pharmaceutical product, providing information for moving the robotic arm, and/or confirming placement of the product. The suction element 19 is preferably comprised of a compressible material which conforms to a surface of a solid pharmaceutical or nutraceutical product. This suction element may be replaced to eliminate concerns about cross-contamination when the system is used with multiple patients. Alternately, known robotic pick and place physical gripping elements may also be utilized. In such an alternate embodiment, these physical structures may also be replaceable and/or washable for eliminating cross-contamination concerns.

The camera element 17 may also be used to confirm that a solid pharmaceutical product that is received from a bulk container corresponds with the expected physical characteristics of the expected solid pharmaceutical product. This aspect of the invention provides additional assurance against prescription filling errors.

Figure 5:
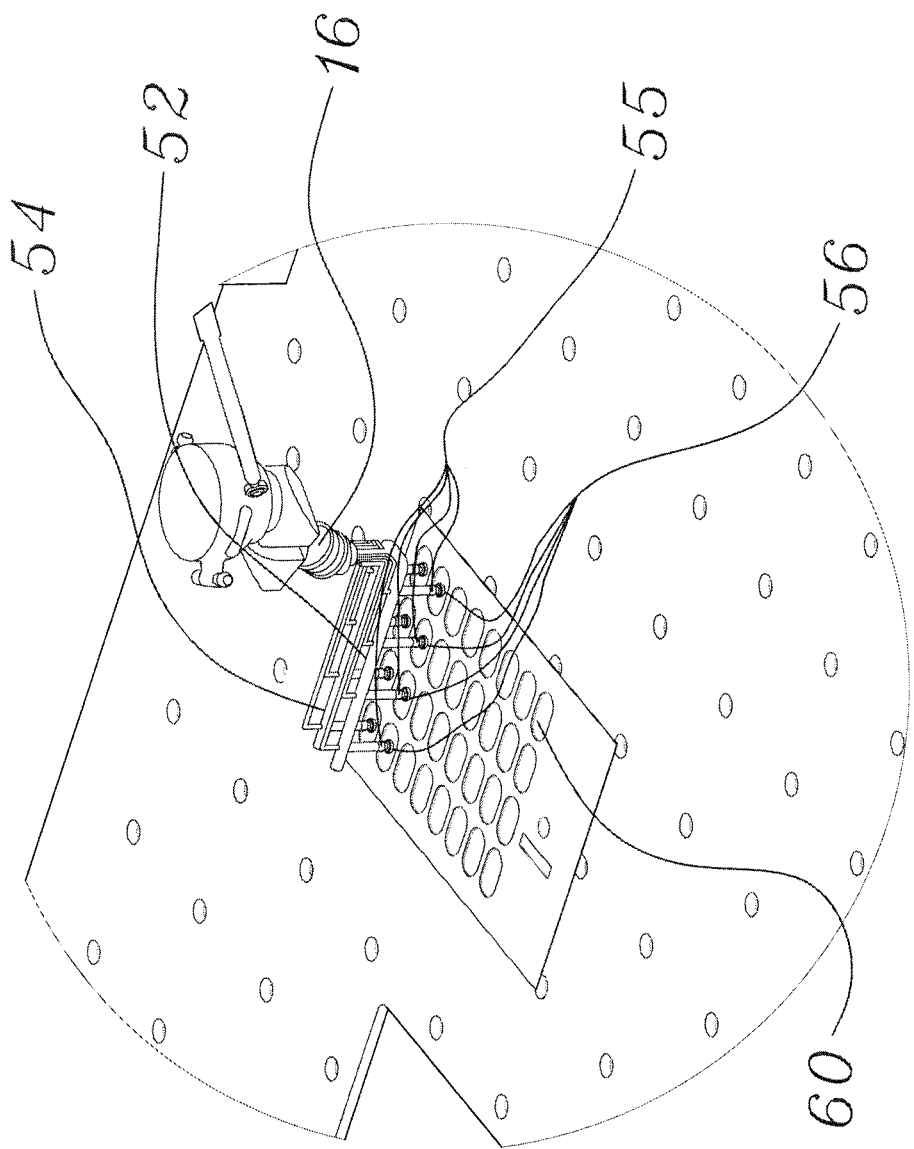
FIG. 5 illustrates an alternate embodiment of the present invention wherein a single robotic arm includes plural pick and place structures spaced corresponding to different locations of solid pharmaceutical product packaging.

FIG. 5 illustrates an alternate preferred exemplary embodiment of the present invention which illustrates the simultaneous transfer of a plurality of solid pharmaceuticals from a bulk storage into the product package cavities during a single movement of the suction arm from the bulk storage to the package. As illustrated in FIG. 5, the robotic joint 16 incorporates a modified suction arm having at least first and second segments 52, 54 which each preferably have a plurality of suction locations 55 which temporarily secure corresponding solid pharmaceuticals 56. Advantageously, by providing the appropriate spacing for the solid pharmaceuticals when secured to the suction locations 55 in correspondence with the cavities 60 of the product package that is to be filled, the number of transfer movements for the robotic arm can be substantially reduced.

In accordance with a preferred embodiment of the invention, the suction arm members or at least the portions thereof which are physical contact with the solid pharmaceuticals are either formed of a lightweight disposable plastic material that can easily be replaced by the system operator. The cleaning or replacing of these system elements also reduces cross-contamination concerns.

The structures illustrated in FIG. 5 may be comprised of telescoping structures that are extendable via operation of servo motors in order to provide the appropriate physical relationship between a plurality of individual grabbing or sucking elements located on the telescoping structure and the product package cavities and/or pharmaceuticals in the bulk containers or other locations for the solid pharmaceuticals.

Figure 6:
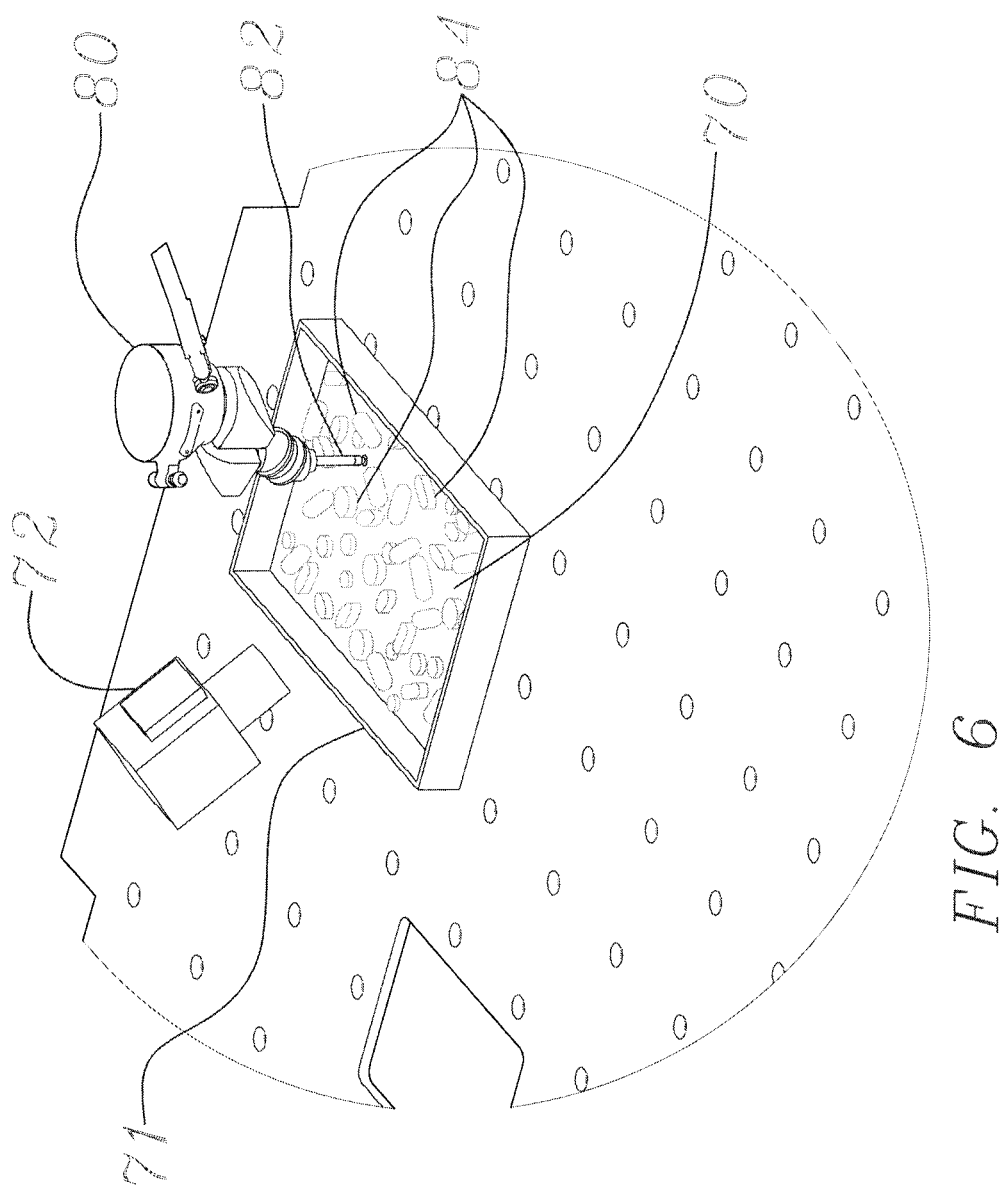
FIG. 6 illustrates an alternate embodiment of the present invention wherein the robotic pick and place system is used in identifying a plurality of different medications.

FIG. 6 illustrates another alternate preferred exemplary embodiment of the system. In this alternate embodiment, a flat surface or table 70 may be provided adjacent to or at the location of the product package filling location. In accordance with this alternate embodiment of the present invention, the pharmacist or assistant is able to place a plurality of random pills for identification on the table 70. An imaging system 72 operating in conjunction with a computer having access to a database of solid pharmaceutical product physical characteristics compares the imaged physical characteristics of the solid pharmaceutical products to be identified 84 so that the products can be automatically identified. The identified products may then be placed in packaging and tagged with a label automatically via the robotic pick and place unit 80 and suction arm 82.

In those instances where image information alone is inadequate to confirm pill identification, the robotic arm may place the pill proximate a source of radiation such as, for example, a laser or NIR for performing spectrographic analysis of the pills in order to provide verifications of the chemical components of the solid pharmaceutical product. In this embodiment, a database of information provides correlation between chemical analysis and solid pharmaceutical products so that is possible to confirm the identity of the solid pharmaceutical product that is being package by the system.

Figure 7:
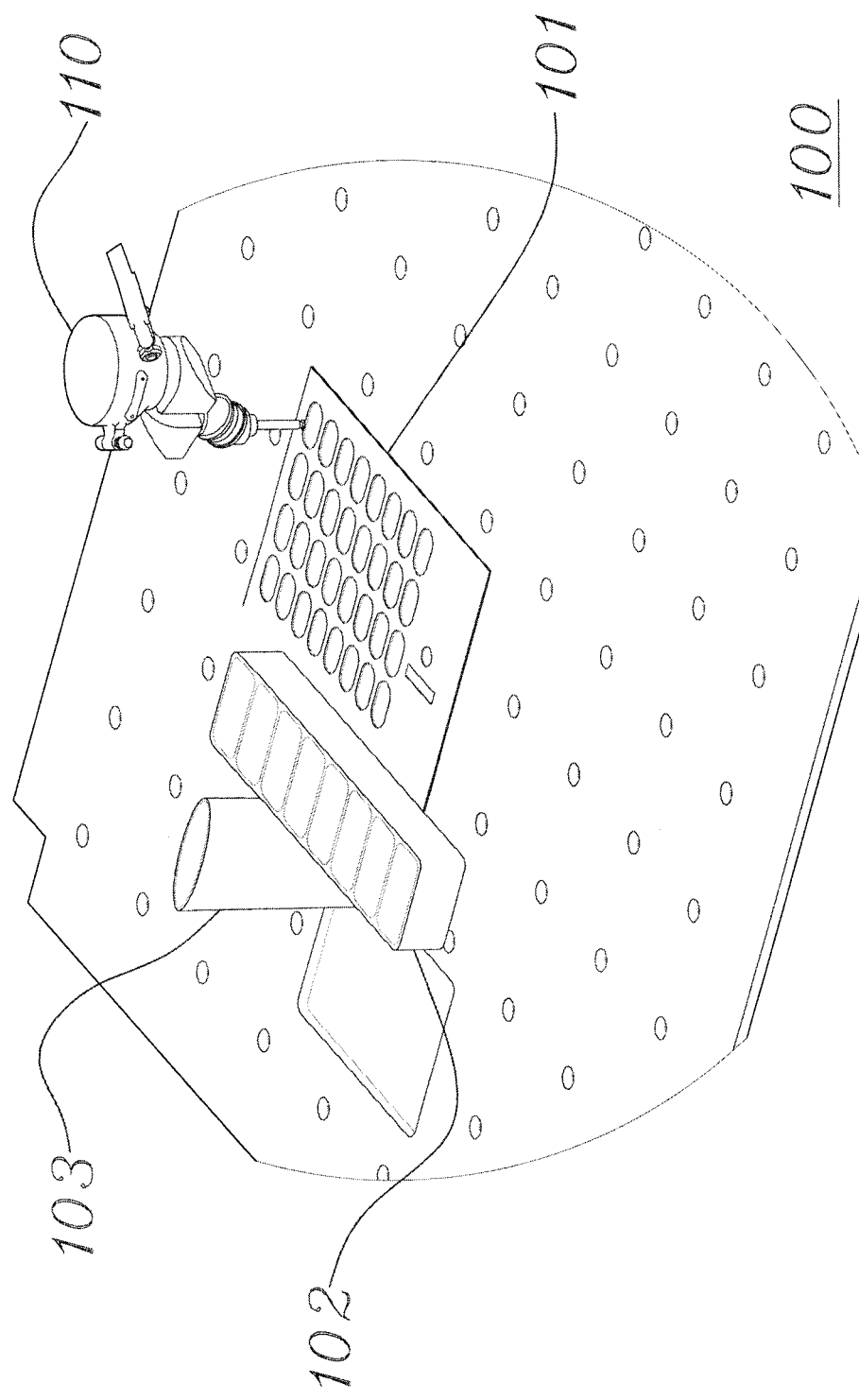
FIG. 7 illustrates an alternate embodiment of the present invention wherein different packaging solutions are alternately selected.

FIG. 7 illustrates another alternate preferred exemplary embodiment of the present invention. In this alternate embodiment, the pick and place robot 110 selectively transfers a desired solid pharmaceutical product package from a storage location to a filling location based upon user selection. Specifically, the robot 110 is able to select any one of the package style 101, 102 and a conventional pill vial 103 for filling by the system. As a result of this mode of operation, the patient is able to initially receive prescribed solid pharmaceutical product package in a desired format without having to transfer from an initially received pill vial.

Figure 8:
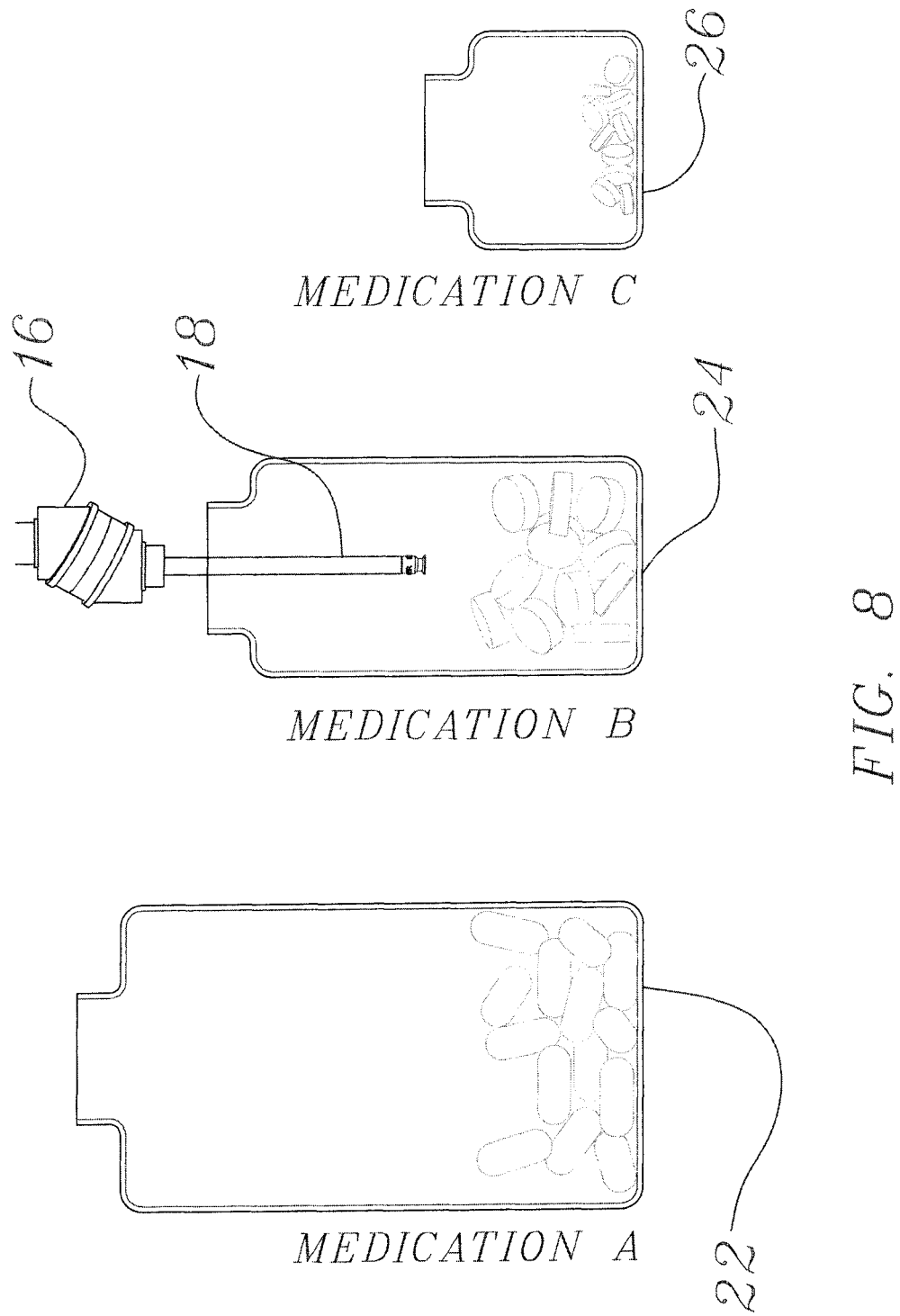
FIG. 8 illustrates a preferred embodiment of the present invention wherein individual pharmaceutical products are transferred from bulk containers.

FIG. 8 illustrates the detailed operation of the interaction between the robotic arm and suction arm 18 and the bulk solid pharmaceutical containers 22, 24, 26, as illustrated. As described above, the computer controller selects the appropriate medication for transfer and the suction arm is selectively positioned in the prescribed bulk storage for transfer of the appropriate medicine into the product package.

In an alternate embodiment, the system may be utilized for repackaging of a given patient's solid pharmaceutical products. In this mode of operation, the bulk containers may be replaced with individual pill vials containing the prescriptions for a person. In accordance with this version of the system operation, based on known prescription data, an alternate form of packaging may be filled when using the patient's prescription containers as substitutions for the pill containers. Alternatively, the pills from a patient's prescription pill vials may be placed upon the table from the embodiment of the invention described above having the flat surface. The imaging system may be used to select appropriate solid pharmaceuticals from the table for placement in the packaging in accordance with the stored patient prescription data.

Those skilled in the art will appreciate that the present invention has been described with reference to exemplary embodiments which are provided for the sake of illustration. It should be appreciated that one or more of the embodiments may be combined in a single system. The invention is not limited to the specific systems and methods specifically set forth in the instant specification.

I claim:

1. A system for transferring solid pharmaceutical products from a plurality of bulk containers into individual product packages comprising:
   a plurality of bulk containers each having a plurality of solid pharmaceutical products contained therein;
   at least one product package having a plurality of locations for receiving solid pharmaceutical products;
   a computer controlled robotic transfer device for selectively removing and thereafter transferring one or more solid pharmaceutical products from bulk storage locations into one or more product package cavity locations for each individual product package corresponding to electronically stored patient prescription information, wherein the robotic transfer device automatically operates to transfer solid pharmaceutical products form the bulk containers to the at least one product package having a plurality of locations for receiving solid pharmaceutical products and the plurality of locations receive solid pharmaceuticals transferred from the bulk storage locations corresponding to the electronically stored patient prescription information, and further wherein the robotic transfer device simultaneously transfers at least two individual solid pharmaceutical products during a single transfer motion into two corresponding product package locations.

2. The system for transferring solid pharmaceutical products from a plurality of bulk containers into product packaging according to claim 1, wherein the bulk containers, product package and computer controlled robotic transfer device are located within a common housing.

3. The system for transferring solid pharmaceutical products from a plurality of bulk containers into product packaging according to claim 1, wherein the robotic transfer device includes an electronic camera that traverses with the robotic transfer device.

4. The system for transferring solid pharmaceutical products from a plurality of bulk containers into product packaging according to claim 1, further comprising an electronic database containing information concerning physical characteristics for solid pharmaceuticals.

5. The system for transferring solid pharmaceutical products from a plurality of bulk containers into product packaging according to claim 1, further comprising an electronic vision verification system for confirming pill placement in product packaging.

6. The system for transferring solid pharmaceutical products from a plurality of bulk containers into product packaging according to claim 1, wherein the bulk containers are patient prescription vials.

7. A method for transferring solid pharmaceutical products from a plurality of bulk containers into product packaging comprising:
   providing a plurality of bulk containers each having a plurality of solid pharmaceutical products contained therein;
   providing at least one product package having one or more locations for receiving solid pharmaceutical products;
   controlling a computer controlled robotic transfer device for selectively removing and thereafter transferring one or more solid pharmaceutical products from a bulk storage location into one or more product package cavity locations corresponding to electronically stored patient prescription information, wherein the robotic transfer device automatically operates to transfer solid pharmaceutical products form the bulk containers to the at least one product package having a plurality of locations for receiving solid pharmaceutical products and the plurality of locations receive solid pharmaceuticals transferred from the bulk storage locations corresponding to the electronically stored patient prescription information, and further wherein the robotic transfer device simultaneously transfers at least two individual solid pharmaceutical products during a single transfer motion into two corresponding product package locations.

8. The method for transferring solid pharmaceutical products from a plurality of bulk containers into product packaging according to claim 7, wherein the bulk containers, product package and computer controlled robotic transfer device are located within a common housing.

9. The method for transferring solid pharmaceutical products from a plurality of bulk containers into product packaging according to claim 7, further comprising moving the robotic transfer device with an electronic camera that traverses with the robotic transfer device.

10. The method for transferring solid pharmaceutical products from a plurality of bulk containers into product packaging according to claim 7, further comprising storing an electronic database containing information concerning physical characteristics for solid pharmaceuticals and comparing determined physical characteristics of an unknown solid pharmaceutical with the database and identifying the unknown solid pharmaceutical based on the identification.

11. The method for transferring solid pharmaceutical products from a plurality of bulk containers into product packaging according to claim 7, further comprising confirming pill placement in product packaging with an electronic vision verification system.

12. The method for transferring solid pharmaceutical products from a plurality of bulk containers into product packaging according to claim 7, wherein the bulk containers are patient prescription vials.

\* \* \* \* \*